United States Patent
Wada et al.

(10) Patent No.: US 6,863,664 B2
(45) Date of Patent: Mar. 8, 2005

(54) ABSORBENT PAD SUITED FOR USE WITH TAMPON

(75) Inventors: Mitsuhiro Wada, Kagawa (JP); Ayami Suga, Kagawa (JP)

(73) Assignee: Uni-Charm Corporation, Kawanoe (JP)

(*) Notice: Subject to any disclaimer, the term of this patent is extended or adjusted under 35 U.S.C. 154(b) by 629 days.

(21) Appl. No.: 10/054,342

(22) Filed: Nov. 13, 2001

(65) Prior Publication Data
US 2002/0068894 A1 Jun. 6, 2002

(30) Foreign Application Priority Data
Nov. 17, 2000 (JP) ........................................ 2000-350682

(51) Int. Cl.[7] ................................................ A61F 13/15
(52) U.S. Cl. ........................ 604/385.17; 604/385.17; 604/385.01; 604/11
(58) Field of Search ....................... 604/385.17, 385.18, 604/11–14, 385.01

(56) References Cited

U.S. PATENT DOCUMENTS

| 3,037,506 A | 6/1962 | Penksa |
| 3,900,032 A | 8/1975 | Heurlen |
| 6,059,763 A | 5/2000 | Brown |

FOREIGN PATENT DOCUMENTS

| EP | 0201348 | 11/1986 | ........... A61F/13/20 |
| JP | 501322 A | 2/2000 | |
| WO | 93/21880 | 11/1993 | ........... A61F/13/15 |
| WO | WO9808475 | 3/1998 | |

*Primary Examiner*—John J. Calvert
*Assistant Examiner*—Jacqueline F Stephens
(74) *Attorney, Agent, or Firm*—Darby 7 Darby

(57) ABSTRACT

Provided is an absorbent pad for being used with a sanitary tampon, which includes a pad body having liquid absorbency. The pad body has front and rear faces, and a string receiving portion. The string receiving portion passes through from the front face to the rear face so that a string extending from the tampon can be inserted into the string receiving portion.

8 Claims, 1 Drawing Sheet

ABSORBENT PAD SUITED FOR USE WITH TAMPON

BACKGROUND OF THE INVENTION

1. Field of the Invention

The present invention generally relates to an absorbent pad to be used with a sanitary tampon and, more particularly, to an absorbent pad which can be reliably aligned with the tampon.

2. Related Art

The sanitary tampon is often used with an absorbent article such as a sanitary napkin. This is because the menstrual blood, as could not be fully absorbed by the tampon, or the menstrual blood having leaked from the clearance between the tampon and the vaginal cavity may be prevented from staining a wearer's undergarments or other clothing.

With only a small quantity of menstrual blood leaking from the tampon, however, the napkin to be used with the tampon has a relatively large size to give the wearer an uncomfortable feeling. It is also troublesome to wear both the napkin and the tampon.

In Japanese Unexamined Patent Publication (Kohyo) No. 2000-501322, there is disclosed an absorbent article having an absorbent structure which combines the features of both the tampon and the sanitary napkin. This absorbent article is folded along a longitudinal centerline thereof so that the two portions of a backsheet on either side of the longitudinal centerline are brought adjacent to each other. Then, the absorbent article is inserted so that it is worn between the wearer's labia minora and labia majora, and blocks the wearer's vaginal introitus.

However, there is one problem such that it is difficult to find the location of the labia majora of the wearer to fit such a absorbent article in position. Furthermore, there is another problem such that the quantity of menstrual blood to be absorbed by the absorbent article is less than that of the conventional tampon, and the wearer's fingers tend to be stained with the menstrual blood when the absorbent article is to be put on or off.

SUMMARY OF THE INVENTION

The present invention has been worked out in view of the shortcoming in the prior art set forth above. It is therefore an object of the present invention to provide an absorbent pad to be used with a tampon, which can absorb the menstrual blood leaking from the clearance between the tampon and the body of the wearer (i.e., the vaginal cavity) or the menstrual blood not fully absorbed by the tampon, and which is compact and adapted to be worn in position of the body.

According to an aspect of the present invention, an absorbent pad for being used with a tampon comprising:

a pad body having liquid absorbency, the pad body having front and rear faces and a string receiving portion, the string receiving portion passing through from the front face to the rear face so that a string extending from the tampon can be inserted into the string receiving portion.

The absorbent pad has a structure in which the string extending from the tampon can pass through the pad body. Therefore, by means of the string of the tampon, the absorbent pad can be reliably fitted in the vaginal opening in which the tampon is inserted, and the pad body can be avoided the displacement from the fitted position of the tampon while the absorbent pad is worn. As a result, the pad body can reliably absorb the small quantity of menstrual blood, as may leak from the clearance between the tampon and the vaginal cavity, so that it can be made thin and small-sized.

Preferably, the pad body has a guide slit extending from one end of the pad body to the string receiving portion for guiding the string, so that the string can be easily guided into the string receiving portion.

On the other hand, the absorbent pad may further comprise a clamping sheet located on the rear face of the pad body and joined partially to the pad body so that the string extending from the string receiving portion to the rear face of the pad body can be clamped between the pad body and the clamping sheet. Accordingly, the pad body is hardly displaced from the vaginal opening upon wearing the undergarment, and can be easily fitted in position.

Furthermore, it is preferred that the clamping sheet has an area greater or equal to that of the pad body for covering substantially the entire rear face of the pad body.

It is also preferred that the clamping sheet is made liquid-impervious, and that the clamping sheet is treated to have low frictional properties on one side opposite to the other side facing the pad body. This absorbent pad is hardly displaced from the relative position to the tampon so that the rear face of the pad body need not be adhered to the undergarment. Furthermore, the rear face of the clamping sheet may be treated to have the low frictional properties to easily slide on the undergarment. Accordingly, it is possible to avoid displacement of the pad body following displacement of the undergarment even if the undergarment is displaced from the wearer's body.

It is preferred that the rear face of the pad body is made liquid-impervious. On the other hand, the pad body may comprise a liquid pervious topsheet; a liquid impervious backsheet; and absorbent core sandwiched between the topsheet and the backsheet.

BRIEF DESCRIPTION OF THE DRAWINGS

The present invention will be understood more fully from the detailed description given hereinafter and from the accompanying drawings of the preferred embodiment of the present invention, which, however, should not be taken to be limitative to the invention, but are for explanation and understanding only.

In the drawings.

DESCRIPTION OF THE PREFERRED EMBODIMENT

Figure 1:
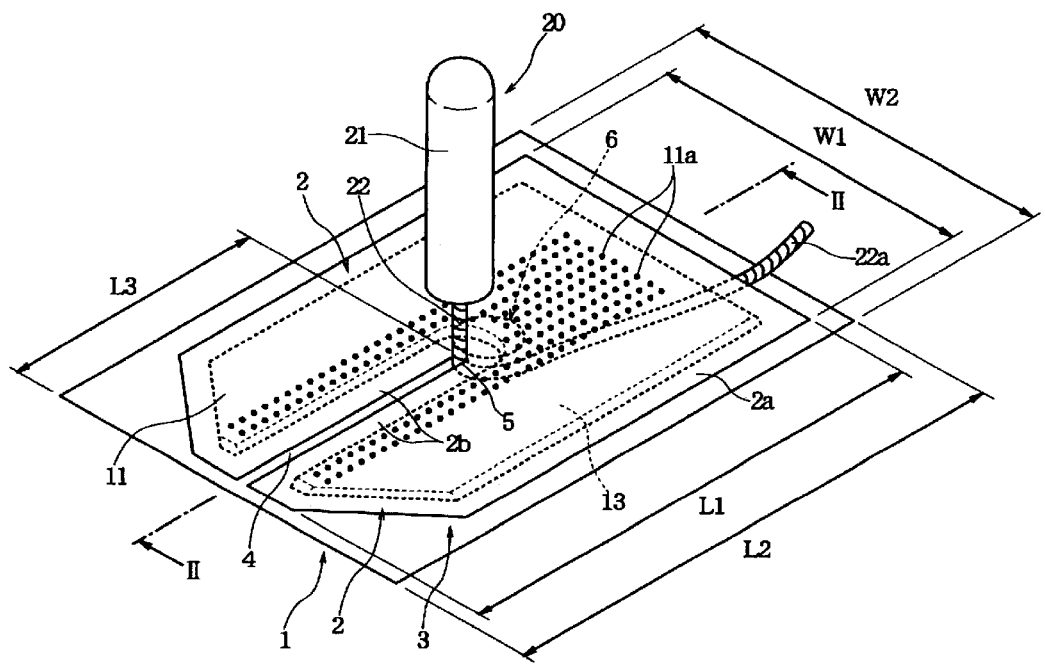
FIG. 1 is a perspective view showing an absorbent pad of the present invention in combination with a sanitary tampon.
Figure 2:
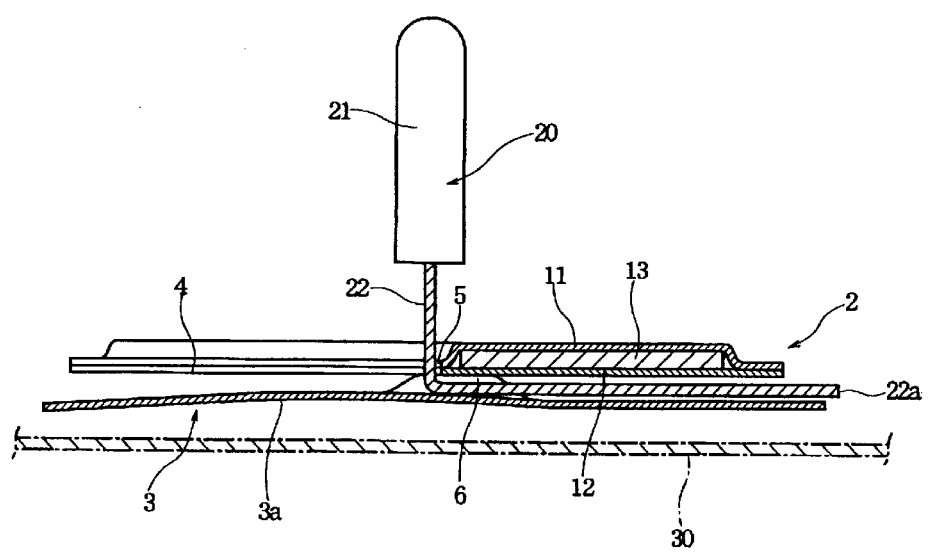
FIG. 2 is a sectional view taken along the line II—II of FIG. 1.

FIG. 1 is a perspective view showing an absorbent pad of the present invention in combination with the conventional sanitary tampon, and FIG. 2 is a sectional view taken along the line II—II of FIG. 1.

As shown in FIGS. 1 and 2, an absorbent pad 1 of the invention is a flat (or planar) pad having liquid absorption capacity (absorbency) and is applicable for use with a tampon 20. The absorbent pad 1 comprises a pad body 2 and a clamping sheet 3 which are partially joined by an adhesive.

As shown in FIG. 2, the pad body 2 includes a liquid pervious topsheet 11, a liquid impervious backsheet 12 and an absorbent core 13 sandwiched between the topsheet 11 and the backsheet 12. The pad body 2 is not provided with the absorbent core 13 about a peripheral portion 2a thereof so that the topsheet 11 and the backsheet 12 are joined to each other with an adhesive. (It should be noted that the peripheral portion 2a is defined by both end edges and side edges of the pad body 2.)

It is preferable that the entire pad body 2 is made of a water-decomposable (or water-disintegrated) material, and that the adhesive is water-soluble. With such a construction, the absorbent pad 1 can be disposed of after use into the flush toilet. It should be noted that the pad body 2 may not be made of such water-decomposable material.

In the pad body 2, there is formed a guide slit 4 which extends from one side (i.e., a front end) to a generally central portion of the pad body 2. The guide slit 4 is terminated at a string receiving portion (or a string receptacle) 5 which extends from a front face (or a body surface) to a rear face (or a garment surface) of the pad body 2. On the other hand, the absorbent core 13 is not provided at a region 2b which surrounds the guide slit 4 and the string receiving portion 5 so that the topsheet 11 and the backsheet 12 are joined to each other. In other words, the joined portion between the topsheet 11 and the backsheet 12 is cut to define the guide slit 4 and the string receiving portion 5.

In the topsheet 11, as shown in FIG. 1, there are formed a plurality of apertures 11a which are located in the vicinity of the region 2b (that is, the apertures 11a are not formed on both longitudinal side portions of the topsheet 11).

The backsheet 12 of the pad body 2 and the clamping sheet 3 are partially joined to each other at a joined portion 6 by means of an adhesive. This joined portion 6 is formed in the vicinity of the string receiving portion 5 but does not overlap the string receiving portion 5. In other words, the backsheet 12 is not joined to the clamping sheet 3 using the adhesive except for the joined portion 6.

The clamping sheet 3 is preferred to be made of paper, nonwoven fabric or a film and to be liquid-impervious. A rear face 3a of the clamping sheet 3 is not provided with an adhesive layer to be adhered to an undergarment 30. The whole area of the rear face 3a is treated to have low frictional properties. This treatment comprises coating of the rear face 3a with a silicone resin, a fluorine resin or the like.

The pad body 2 is smaller than the sanitary napkin of the prior art, and is of such size as to reliably block the vaginal opening (or vaginal introitus) without any deflection when worn. For example, the pad body 2 is preferred to have the largest length L1 of about 80 to 130 mm, preferably 100 to 120 mm in a longitudinal direction and the maximum width W1 of 50 to 80 mm, preferably about 60 to 70 mm. (The term "longitudinal", as used herein, refers to a direction in the plane of the pad body 2 that is generally aligned with a vertical plane which bisects a standing wearer into left and right body halves when the pad body 2 is worn.)

The clamping sheet 3 may overlap at least partially the rear face of the pad body 2, but is preferred to have the same size as that of the pad body 2 or to be larger than the pad body 2 as shown in FIG. 1, so that the entire rear face of the pad body 2 can be covered by the clamping sheet 3. If the clamping sheet 3 is thus made liquid-impervious and covers the entire rear face of the pad body 2, it is possible to prevent the undergarment from being stained with the menstrual blood by means of the clamping sheet even if the menstrual blood leaks from the pad body 2.

For example, it is preferred that the clamping sheet 3 has a length L2 of about 85 to 140 mm in the longitudinal direction thereof, which is larger than the length L1 of the pad body 2, and the clamping sheet 3 also has a width W2 of about 55 to 90 mm.

It is also preferred that the string receiving portion 5 is located at the generally central portion of the pad body 2, and that the guide slit 4 has a length L3 of about one third to one half of the length L1 of the pad body 2.

Next, a method for fitting the tampon 20 and the absorbent pad 1 to the wearer's body will be described hereinafter.

The tampon 20 comprises a compressed absorber or absorbent body 21 and a string or lead 22 extending from the absorber 21. The absorber 21 may be accommodated within an applicator or may not be accommodated within an applicator (i.e., the absorber 21 may be a finger type tampon).

The tampon 20 is inserted into the vaginal cavity, and then the applicator is pulled out. After that, the string 22 is inserted into the guide slit 4 of the pad body 2 and is guided along the guide slit 4 into the string receiving portion 5 (between the pad body 2 and the clamping sheet 3). When an end portion 22a of the string 22 is then grasped to pull up the pad body 2, the pad body 2 is fitted in the vaginal opening by the guiding action (or guiding means) of the string receiving portion 5 and the string 22. It should be noted that the absorbent pad 1 is fitted to the wearer's body so that the front end having the guide slit 4 is oriented forwardly of the wearer's body.

After the pad body 2 was fitted in the vaginal opening, the string 22 is held between the pad body 2 and the clamping sheet 3. For example, the string 22 may be clamped between the pad body 2 and the clamping sheet 3, after moving the end portion 22a of the string 22 on the opposite side of the guide slit 4, as shown in FIG. 1.

Since the string 22 is thus clamped between the pad body 2 and the clamping sheet 3, the pad body 2 is hardly displaced from the vaginal opening before and after wearing the undergarment.

Furthermore, the clamping sheet 3 has no adhesive layer on the rear face 3a thereof, and is not adhered to the undergarment 30. Accordingly, the clamping sheet 3 can move relatively to the undergarment 30. In particular, in the case where the rear face 3a of the clamping sheet 3 is treated to have low frictional properties, the clamping sheet 3 can slide relatively to the undergarment 30 upon displacement of the undergarment 30 thereby to prevent the pad body 2 from being out of the vaginal opening.

A small quantity of menstrual blood, as having leaked from the absorber 21 of the tampon, is absorbed by the absorbent core 13 of the pad body 2. The body surface of the topsheet 11 of the pad body 2 to be located adjacent to the absorber 21, has the plurality of apertures 11a so that the menstrual blood having leaked from the tampon 20 is promptly absorbed by the absorbent core 13. On the other hand, even if the menstrual blood runs down through the string 22, it is possible to prevent the undergarment 30 from being stained with the menstrual blood, because the string 22 is held between the pad body 2 and the clamping sheet 3, and the clamping sheet 3 is further made liquid-impervious.

The topsheet 11 may be formed of a liquid pervious nonwoven fabric or a resin film having apertures, and may be also made of a water-decomposable sheet. On the other hand, the backsheet 12 and the clamping sheet 3 are made of a liquid impervious sheet of nonwoven fabric or paper which is composed essentially of hydrophobic fibers, or a resin film, and may be also formed of a water-decomposable sheet.

For example, the topsheet 11, the backsheet 12 and the clamping sheet 3 may be made of water-decomposable paper formed into a sheet by hydrogen-bonding pulp fibers; water-decomposable paper made of water-dispersible fibers of pulp or rayon and a water-soluble binder; or nonwoven fabric having hydrophilic fibers entangled into a water-dispersible state. On the other hand, the backsheet 12 and the clamping sheet 3 may be made of a liquid impervious water-decomposable sheet prepared by coating the water-decomposable paper or nonwoven fabric with a water-soluble resin such as copolymer of polyvinyl alcohol and an unsaturated carboxylic acid.

The absorbent core 13 maybe formed of water-decomposable paper, pulp or nonwoven fabric. For example, this material is exemplified by a plurality of laminated sheets of relatively thin water-decomposable paper, or air-laid pulp.

The pad body 2 of the invention is not be limited to the laminated or layered structure of the topsheet 11, the backsheet 12 and the absorbent core 13 as set forth above. In other words, the pad body 2 can be made to have a simple pad structure because the small quantity of menstrual blood (i.e., the menstrual blood which could not be fully absorbed by the tampon or the menstrual blood which has leaked from the clearance between the vaginal opening and the tampon) may be exclusively absorbed by the pad body 2. For example, the pad body 2 may be composed exclusively of the backsheet 12 and the absorbent core 13 while eliminating the topsheet 11, as exemplified by the pad body 2 formed of only water-decomposable paper and a PVA (polyvinyl alcohol) film. Furthermore, it is desirable that at least one of the rear face of the pad body 2 and the clamping sheet 3 may be made liquid-impervious.

Alternatively, the absorbent pad 1 may comprise only pad body 2 without providing the clamping sheet 3. On the other hand, the pad body 2 may have a hole or a slit through which the string 22 can be inserted by the fingers of a user, in place of the guide slit 4. Furthermore, the pad body 2 need not be hexagonal as shown in the embodiment of FIG. 1, but may be made rectangular or elliptical.

As set forth above, the absorbent pad according to the invention can be easily fitted in position of the wearer when being used with the sanitary tampon. On the other hand, the absorbent pad is made to have a smaller size than that of the conventional sanitary napkin so that it gives the wearer less uncomfortable feeling when the absorbent pad is worn in comparison with the sanitary napkin thereby to provide wearing comfort of the absorbent pad. On the other hand, the absorbent pad of the invention can be positioned by means of the string of the tampon so that it is possible to reliably align the absorbent pad with the vaginal opening and to avoid the displacement of the pad while being worn.

Although the present invention has been illustrated and described with respect to exemplary embodiment thereof, it should be understood by those skilled in the art that the foregoing and various other changes, omission and additions may be made therein and thereto, without departing from the spirit and scope of the present invention. Therefore, the present invention should not be understood as limited to the specific embodiment set out above but to include all possible embodiments which can be embodied within a scope encompassed and equivalent thereof with respect to the feature set out in the appended claims.

What is claimed is:

1. An absorbent pad for being used with a tampon comprising:

a pad body having liquid absorbency, said pad body having front and rear faces and a string receiving portion, said string receiving portion passing through from the front face to the rear face so that a string extending from the tampon can be inserted into said string receiving portion.

2. An absorbent pad as set forth in claim 1, wherein said pad body has a guide slit extending from one end of said pad body to said string receiving portion for guiding said string.

3. An absorbent pad as set forth in claim 1, further comprising:

a clamping sheet located on the rear face of said pad body and joined partially to said pad body so that said string extending from said string receiving portion to the rear face of said pad body can be clamped between said pad body and said clamping sheet.

4. An absorbent pad as set forth in claim 3, wherein said clamping sheet has an area greater or equal to that of said pad body for covering substantially the entire rear face of said pad body.

5. An absorbent pad as set forth in claim 3, wherein said clamping sheet is made liquid-impervious.

6. An absorbent pad as set forth in claim 3, wherein said clamping sheet is treated to have low frictional properties on one side opposite to the other side facing said pad body.

7. An absorbent pad as set forth in claim 1, wherein the rear face of said pad body is made liquid-impervious.

8. An absorbent pad as set forth in claim 1, wherein said pad body includes a liquid pervious topsheet, a liquid impervious backsheet, and an absorbent core sandwiched between said topsheet and said backsheet.

\* \* \* \* \*